United States Patent [19]

Chippett et al.

[11] Patent Number: 4,976,922

[45] Date of Patent: Dec. 11, 1990

[54] STERILIZATION METHOD

[75] Inventors: Simon Chippett, Charleston, W. Va.; Stephen A. Conviser, Pelham, N.Y.

[73] Assignee: Union Carbide Corporation, Danbury, Conn.

[21] Appl. No.: 318,767

[22] Filed: Mar. 3, 1989

[51] Int. Cl.⁵ ............................................. A61L 2/20
[52] U.S. Cl. ................................. 422/34; 422/900; 252/372; 514/475
[58] Field of Search ..................... 422/34, 900, 37; 252/372, 386

[56] References Cited

U.S. PATENT DOCUMENTS

| | | | |
|---|---|---|---|
| 2,075,845 | 4/1937 | Gross et al. | 167/39 |
| 3,989,461 | 11/1976 | Skocypec et al. | 422/34 X |
| 4,130,393 | 12/1978 | Fox | 422/34 X |
| 4,555,251 | 11/1985 | Jonsson et al. | 422/34 X |

FOREIGN PATENT DOCUMENTS 1288568  9/1989  United Kingdom ................. 422/34

OTHER PUBLICATIONS

"Ethylene Oxide", Hess, L. G. et al., Industrial & Eng. Chem., vol. 42, No. 6, pp. 1251–1258, Jun. 1950.
"The Merck Index", 10th ed., Merck & Co., Inc., New Jersey, p. 1306 (1983).
Fluorocarbon/Ozone, Dupont "Freon" Products Division, Mar. 1987.
Chemical Marketing Reporter, Schnell Publishing Co., Inc., pp. 1, 3, Oct. 3, 1988.
Chemical Marketing Reporter, Schnell Publishing Co., Inc., pp. 1, 3, 13, Nov. 28, 1988.

Primary Examiner—Robert J. Warden
Assistant Examiner—Jeffrey R. Snay
Attorney, Agent, or Firm—Stanley Ktorides

[57] ABSTRACT

A sterilant mixture comprising 15 to 30 mole percent ethylene oxide and 70 to 85 mole percent 1,1-dichloro-2,2,2-trifluoroethane and/or 1-chloro-1,2,2,2-tetrafluoroethane, and a sterilization method using same.

14 Claims, 3 Drawing Sheets

STERILIZATION METHOD

TECHNICAL FIELD

This invention relates generally to the field of sterilization and more particularly to sterilization based on the use of ethylene oxide.

BACKGROUND ART

Sterilization by the application of boiling water or steam to the article to be sterilized has been carried out for many years. More recently there has arisen in certain fields, such as in medicine and in space exploration, the need to employ a different sterilant because certain articles used in these fields cannot withstand the temperatures or the moisture associated with steam sterilization.

One sterilant that has become widely used is ethylene oxide because not only is it an effective sterilant but also its residues volatize relatively quickly from the article sterilized. Although ethylene oxide may be used by itself to carry out the sterilization, this is generally not done because ethylene oxide is highly flammable. Instead ethylene oxide sterilant is generally used in a mixture with a flame retardant. The flame retardant, however, must complement the properties of the ethylene oxide or the beneficial effects of the ethylene oxide will be lost. Over the last two decades the flame retardant of choice for use with ethylene oxide in a sterilant mixture has been dichlorodifluoromethane, known in the industry as CFC 12. The most commonly used sterilant mixture comprises 27.3 mole percent (12 weight percent) ethylene oxide and 72.7 mole percent (88 weight percent) CFC 12. This mixture is commonly referred to in the industry as 12-88.

Recently a problem has arisen in the use of CFC 12 because it is one of the chlorofluorocarbons believed to cause significant damage to the ozone layer in the upper atmosphere. Accordingly worldwide reduction and elimination of the use of CFC 12 is now underway. This has created a problem for the use of ethylene oxide as a sterilant.

As mentioned above, ethylene oxide may be used by itself as a sterilant. However the explosion danger of such use makes it acceptable for only a relatively few applications at locations which have experienced and sophisticated handlers available at all times.

One flame retardant which is known for use with ethylene oxide is carbon dioxide. However because of the characteristics of carbon dioxide, a nonflammable ethylene oxide carbon dioxide mixture contains less than 40 percent of the ethylene oxide per unit volume as does 12-88. Thus, sterilization must be carried out either at higher pressures or for longer contact times. Furthermore the large difference in the vapor pressures of ethylene oxide and carbon dioxide causes the mixture to separate upon withdrawal from the storage tank or cylinder, raising the danger of delivering a sterilant mixture rich in carbon dioxide, which won't sterilize, or rich in ethylene oxide, which is explosive.

Accordingly it is an object of this invention to provide an improved sterilant mixture employing ethylene oxide which overcomes the deficiencies of the known sterilants.

It is another object of this invention to provide an improved sterilization method using a sterilant mixture employing ethylene oxide which overcomes the deficiencies of the known sterilization methods.

SUMMARY OF THE INVENTION

The above and other objects which will become apparent to one skilled in the art upon a reading of this disclosure are attained by the present invention, one aspect of which is:

A sterilant mixture comprising from 15 to 30 mole percent ethylene oxide and from 70 to 85 mole percent 1,1-dichloro-2,2,2-trifluoroethane and/or 1-chloro-1,2,2,2-tetrafluoroethane.

Another aspect of the invention is:

A method for sterilizing an article comprising contacting the article with an effective amount of a sterilant mixture comprising from 15 to 30 mole percent ethylene oxide and from 70 to 85 mole percent 1,1-dichloro-2,2,2-trifluoroethane and/or 1-chloro-1,2,2,2-tetrafluoroethane.

DETAILED DESCRIPTION

Figure 1:
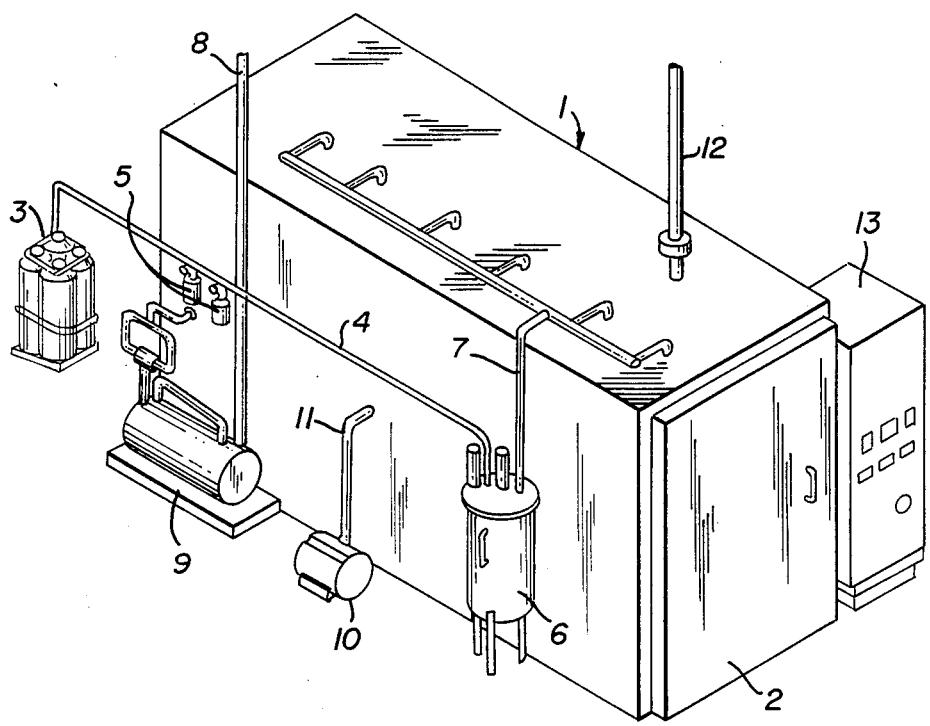
FIG. 1 is a schematic representation of one sterilizer apparatus with which the method of this invention may be employed.

The invention is a sterilant mixture and a method of sterilizing articles using the sterilant mixture. The sterilant mixture is generally used as a gas or vapor.

The sterilant mixture of this invention comprises from 15 to 30 mole percent, preferably from 20 to 26 mole percent, ethylene oxide and from 70 to 85 mole percent, preferably from 74 to 80 mole percent, 1,1-dichloro-2,2,2-trifluoroethane and/or 1-chloro-1,2,2,2-tetrafluoroethane. The ethylene oxide acts as the active sterilizer while the halogenated compound, or compounds if a mixture is employed, acts as a flame retardant. At flame retardant concentrations less than the specified minimum, sufficient flame retardency may not be present in the mixture to avoid a potentially dangerous situation, and at flame retardant concentrations greater than the specified maximum, effective sterilization may not be possible without the use of undesirably high temperatures, pressures and/or contact times. The industrial shorthand term for 1,1-dichloro-2,2,2-trifluoroethane is CFC 123 and the industrial shorthand term for 1-chloro-1,2,2,2-tetrafluoroethane is CFC 124.

Preferably the sterilant mixture of this invention comprises only ethylene oxide and one or both of CFC 123 and CFC 124. However, the sterilant mixture may in addition contain chlorodifluoromethane to increase the vapor pressure or reduce the cost of the sterilant mixture. An increased vapor pressure may be desirable in some sterilization systems to propel the sterilant mixture into the sterilization chamber in a timely manner, particularly in a situation where the sterilant container temperature cannot be maintained at or about 70° F.

Other components which may be present in the sterilant mixture of this invention include inert nitrogen gas which may also be used to increase the pressure in the sterilant container in order to propel the sterilant mixture into the sterilization chamber.

The sterilant mixture of this invention may be used to sterilize a great many articles. Examples of medical equipment and materials which may be sterilized include diagnostic endoscopes; plastic goods such as syringes, gloves, test tubes, incubators and pacemakers; rubber goods such as tubing, catheters and sheeting; instruments such as needles, scalpels and oxygen tests; and other items such as dilators, pumps, motors and intraocular lenses. In addition the sterilant mixture of this invention may be used as a fumigant for items outside the medical field. These items include certain foodstuffs such as spices; furs, bedding, paper goods, and transportation equipment such as the cargo area of airplanes, trains and ships.

The sterilant mixture of this invention is effective against all forms of life, particularly unwanted insects, bacteria, virus, molds, fungi, and other microorganisms. Among the most difficult organisms to kill is B. Subtilus sbs. niger spores; however, even these organisms are effectively destroyed by the sterilant mixture of the invention.

The sterilant mixture of this invention may be made up of using any effective mixing technique well known to those skilled in the art. For example, each compound of the mixture may be pumped gravimetrically through a manifold into a sterilant container, and the container rolled to intermix the compounds into a homogeneous mixture. Alternatively the compounds may be pumped into a mixing tank, recirculated in the tank until a fully homogeneous mixture is formed, and then pumped from the mixing tank into a sterilant container.

The sterilant mixture of this invention may be packaged in any gas storage containers of suitable design such as U.S. Dept. of Transportation (DOT) Specification Nos. 4BA 240, 4BA 300, 4BW 240 or other DOT specification cylinders or trailers of suitable working pressure. The sterilant mixture may also be packaged in American Society of Mechanical Engineers (ASME) storage vessels.

The gas storage cylinder may be delivered to the use site holding the sterilant mixture at a pressure generally within the range of from about 30 to 50 pounds per square inch absolute (psia) at 70° F., and connected through a series of valves, control valves, vaporizer and appropriate conduit to a sterilizer to carry out the sterilization.

The gas mixture of this invention may be used with any commonly employed sterilizer known to the art. One such sterilizer is shown in schematic form in FIG. 1.

Referring now to FIG. 1, the item or items to be sterilized are placed within sterilization chamber 1 through door 2. Sterilizers such as is illustrated in FIG. 1 may range in size from desk-top models to room-size models and even larger. After the items are placed within sterilization chamber 1 and door 2 is shut, the chamber is heated generally to a temperature within the range of from 130° F. to 140° F. Generally the higher the temperature the shorter is the required exposure time. After the chamber is brought up to temperature, a partial vacuum is drawn inside the chamber by pumping out air through vent 8 by vacuum pump 9. The air removal serves both to prevent dilution of the sterilant mixture and to reduce the exposure pressure. Creating the appropriate vacuum generally takes from about 5 to 45 minutes depending on the item to be sterilized since some items can be damaged by sudden pressure changes. Since a moist microorganism is more susceptible to the action of the sterilant, water vapor is employed. In FIG. 1, water vapor from steam source 10 may be injected into chamber 1 through conduit 11. The water vapor is used to create a relative humidity within the chamber within the range of from 30 to 80 percent.

Sterilant mixture is passed from a source such as cylinder 3 through conduit 4 and filters 5 to vaporizer 6 wherein it is converted to a vapor. From vaporizer 6 the sterilant mixture is passed through conduit 7 into sterilization chamber 1 for the sterilization. The pressure at which the sterilization takes place within chamber 1 may be from about 7 to 33 psia. The sterilization time will vary and is dependent upon a number of factors including temperature, pressure, humidity level, the specific sterilant mixture employed, and the material being sterilized. For example, some porous articles require shorter exposure time than do articles sealed in polyethylene bags. Moreover, some bacteria are especially resistant and thus take longer to destroy.

Following the required exposure time, the sterilant mixture is evacuated from the chamber by flushing with air, nitrogen, steam or carbon dioxide through inlet 12 and successive evacuation through conduit 8 by pump 9. The sterilized material is then removed from chamber 1 through door 2 and, if necessary, aerated for the removal of residual sterilant, before being used. The entire sterilization procedure may be monitored and controlled through control panel 13.

The following examples and comparative examples serve to further illustrate or distinguish the invention. They are not intended to be limiting.

Figure 2:
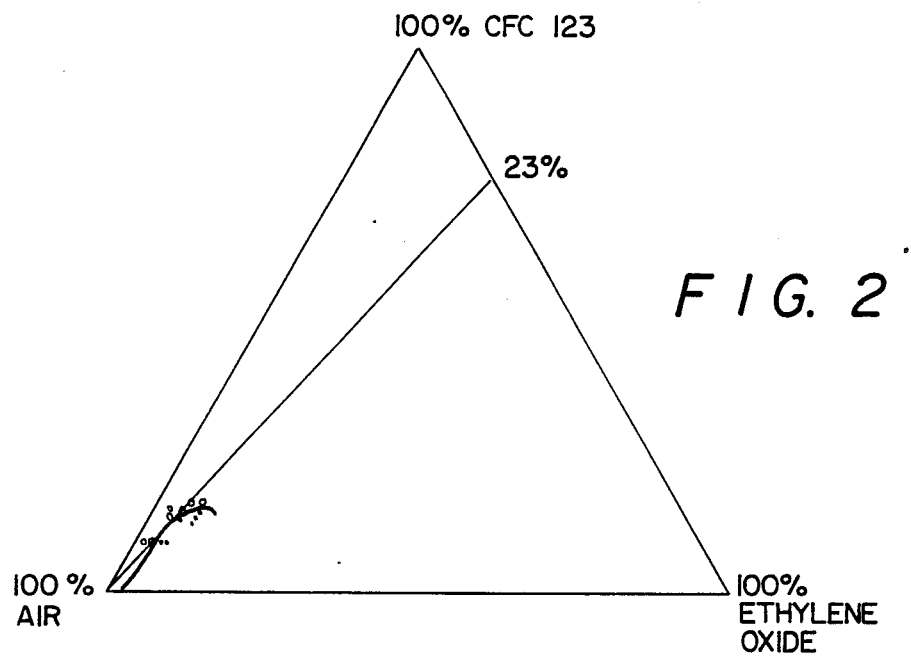
FIG. 2 is a graphical representation of flammability tests for one embodiment of the sterilant mixture of this invention.
Figure 3:
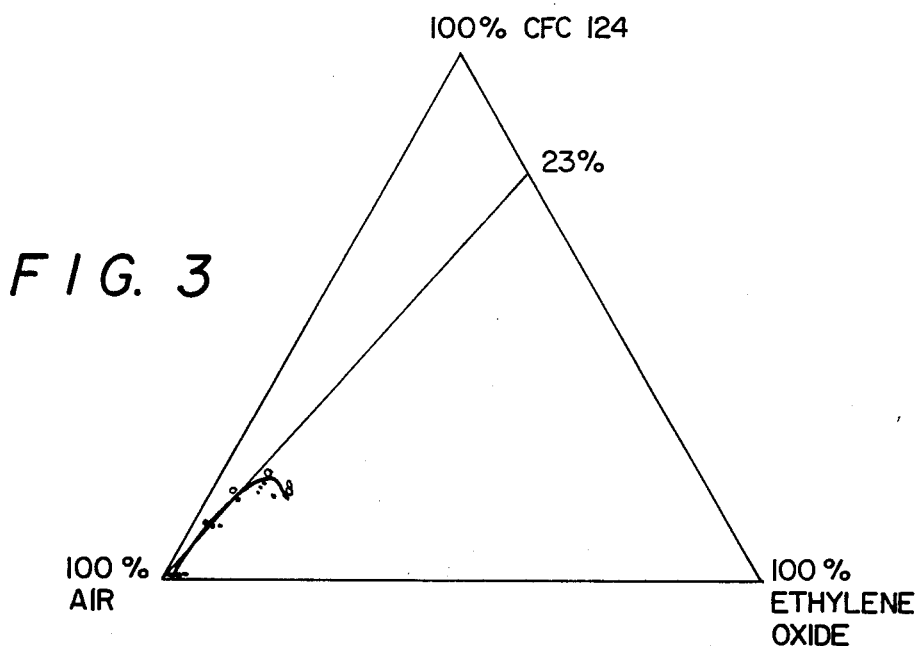
FIG. 3 is a graphical representation of flammability tests for another embodiment of the sterilant mixture of this invention.

A series of flammability tests were carried out to determine the flammability curves for ethylene oxide intermixed respectively with CFC 123 and with CFC 124. The procedure was as follows. Ethylene oxide, air and the flame retardant, all at measured concentrations, were mixed in a 5 liter spherical vessel at 1 atmosphere and 45° C. A hot nichrome wire was placed in the middle of the vessel to provide ignition energy to the mixture. Flame propagation, i.e. whether or not the mixture ignited and the flame propagated, was determined by temperature and pressure sensors on the vessel wall. The data for various mixtures is shown on FIG. 2 for the CFC 123 mixtures and on FIG. 3 for the CFC 124 mixtures. A clear data point indicates no ignition while a solid data point indicates ignition for that particular mixture. The curves shown in FIGS. 2 and 3 represent the flammability curves for each mixture.

In order for a sterilant mixture to be non-flammable it must be non-flammable at all concentrations of air, i.e. from 0 to 100 percent air. Thus a straight line representing 0 to 100 percent air cannot cross below the flammability curve. A straight line from 0 to 100 percent air just tangent to but not crossing below the flammability curve represents the highest ethylene oxide concentration while maintaining the mixture non-flammable. Such straight lines are drawn in FIGS. 2 and 3 and show that for both ethylene oxide/CFC 123 and ethylene oxide/CFC 124 mixtures, the ethylene oxide concentrations can be up to 23 mole percent and yet the mixture remains non-flammable for all concentrations of air.

Figure 4:
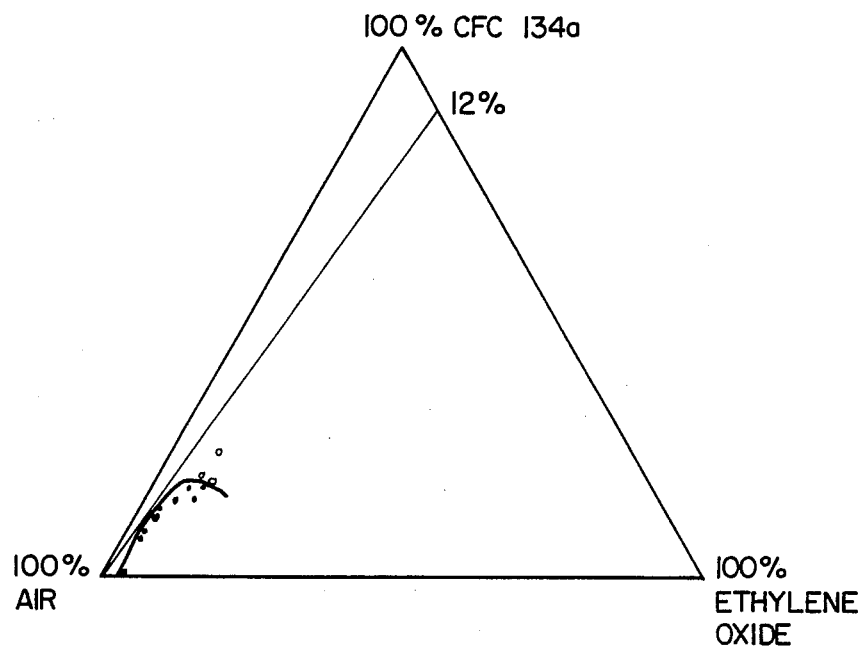
FIG. 4 is a graphical representation of flammability tests for an ethylene oxide mixture formulated with the compound generally accepted as the substitute for CFC 12.

For comparative purposes, the above-described procedure was repeated except that 1,2,2,2-tetrafluoroethane (CFC 134a) was used in place of CFC 123 and CFC 124. CFC 134a has become generally accepted as the most likely replacement for CFC 12. This data is reported in FIG. 4. As is shown by the data, a mixture of ethylene oxide and CFC 134a is non-flammable only up to a maximum ethylene oxide concentration of 12 percent over the full range of air concentration.

The above examples and comparative example serve to demonstrate that the sterilant gas mixtures of the present invention exhibit a non-flammability nearly double that of the mixture formulated with the widely acknowledged replacement for CFC 12.

We claim:

1. A method for sterilizing an article comprising contacting the article with an effective amount of a sterilant mixture comprising from 15 to 30 mole percent ethylene oxide and from 70 to 85 mole percent 1-chloro-1,2,2,2-tetrafluoro-ethane.

2. The method of claim 1 wherein the sterilant mixture has a concentration of ethylene oxide of from 20 to 26 percent.

3. The method of claim 1 wherein the 1-chloro-1,2,2,2-tetrafluoro-ethane has a concentration of from 74 to 80 mole percent.

4. The method of claim 1 wherein the sterilant mixture further comprises chlorodifluoromethane.

5. The method of claim 1 wherein the sterilant mixture further comprises nitrogen.

6. The method of claim 1 wherein the sterilant mixture is in gaseous form when it contacts the article.

7. The method of claim 1 wherein the ethylene oxide concentration is not more than 23 mole percent and the sterilant mixture is not flammable in any concentration of air.

8. A method for sterilizing an article comprising contacting the article with an effective amount of a sterilant mixture comprising from 15 to 30 mole percent ethylene oxide and from 70 to 85 mole percent of a mixture of 1,1-dichloro-2,2,2-trifluoroethane and 1-chloro-1,2,2,2-tetrafluoroethane.

9. The method of claim 8 wherein the sterilant mixture has a concentration of ethylene oxide of from 20 to 26 mole percent.

10. The method of claim 8 wherein the mixture of 1,1-dichloro-2,2,2-trifluoroethane and 1-chloro-1,2,2,2-tetrafluoroethane has concentration of from 74 to 80 mole percent.

11. The method of claim 8 wherein the sterilant mixture further comprises chlorodifluoromethane.

12. The method of claim 8 wherein the sterilant mixture further comprises nitrogen.

13. The method of claim 8 wherein the sterilant mixture is in gaseous form when it contacts the article.

14. The method of claim 8 wherein the ethylene oxide concentration is not more than 23 mole percent and the sterilant mixture is not flammable in any concentration of air.

* * * * *